United States Patent [19]

McCann et al.

[11] Patent Number: 5,373,005

[45] Date of Patent: Dec. 13, 1994

[54] DESPIRAMINE IN THE TREATMENT OF DRUG-RESISTANT MALARIAL INFECTIONS

[75] Inventors: Peter P. McCann, Lenexa, Kans.; Albert Sjoerdsma, Cincinnati; Alan J. Bitonti, Maineville, both of Ohio

[73] Assignee: Merrell Dow Pharmaceuticals Inc., Cincinnati, Ohio

[21] Appl. No.: 26,950

[22] Filed: Mar. 5, 1993

Related U.S. Application Data

[63] Continuation-in-part of Ser. No. 925,703, Aug. 4, 1992, abandoned, which is a continuation-in-part of Ser. No. 725,940, Jun. 27, 1991, abandoned, which is a continuation of Ser. No. 590,437, Sep. 26, 1990, abandoned, which is a continuation of Ser. No. 333,156, Apr. 4, 1989, abandoned, which is a continuation-in-part of Ser. No. 243,524, Sep. 12, 1988, abandoned, which is a continuation-in-part of Ser. No. 183,858, Apr. 20, 1988, abandoned.

[51] Int. Cl.$^5$ .................... A61K 31/55; A61K 31/47
[52] U.S. Cl. .................... 514/217; 514/313
[58] Field of Search .................... 514/297, 313, 217

Primary Examiner—Jerome D. Goldberg
Attorney, Agent, or Firm—Stephen L. Nesbitt

[57] ABSTRACT

Drug-resistant malarial infection in humans can be effectively treated with standard antimalarial agents if administered in conjunction with desipramine.

1 Claim, 7 Drawing Sheets

DESPIRAMINE IN THE TREATMENT OF DRUG-RESISTANT MALARIAL INFECTIONS

This is a continuation-in-part of application Ser. No. 07/925,703, filed Aug. 4, 1992, which is a continuation-in-part of application Ser. No. 07/725,940, filed Jun. 27, 1991, now abandoned, which is a continuation of application Ser. No. 07/590,437, filed Sep. 26, 1990, now abandoned, which is a continuation of application Ser. No. 07/333,156, filed Apr. 4, 1989, now abandoned, which is a continuation-in-part of application Ser. No. 07/243,524, filed Sep. 12, 1988, now abandoned, which is a continuation-in-part of application Ser. No. 07/183,858, filed Apr. 20, 1988, now abandoned.

This invention relates to the use of desipramine in the treatment of drug-resistant Plasmodium infections.

BACKGROUND OF THE INVENTION

Malaria remains a significant health threat to humans despite massive international attempts to eradicate the disease. Over 200 million people are said to have malaria and over one million deaths per year are associated with malaria in Africa alone. In many of the endemic areas, local supply of food is quite limited, a problem which is greatly aggravated by the presence of protozoal infections in cattle and other farm animals. Malaria is a disease of warm blooded animals caused by infection with a parasite of the genus Plasmodium. Four species, P. vivax, P. falciparum, P. malariae, and P. ovale, are known to infect humans. The parasite is transmitted to humans by the bite of Anopheles mosquitoes. Subsequent to mosquito bite, the parasite rapidly invades the blood cells of the victim and after a incubation period, generally lasting about 10 to 14 days, symptoms, consisting of chills, fever, headache, muscle pains, splenomegaly, and anemia, appear. This incubation period may be prolonged for many weeks and onset can be quite insidious. Red blood cells are at first altered and later destroyed by the infection.

Drug therapy utilizing quinine, chloroquine, amodiaquine, primaquine, and other agents has been the mainstay of therapy against malaria. However, drug-resistant strains of plasmodia have developed and in some cases strains are resistant to many or all of the current therapeutic agents. In particular, P. falciparum malaria is quite prone to exhibit single and even multiple drug-resistance. While new agents are continually developed and introduced, resistance to such new agents also quickly develops. For example mefloquine-resistant malaria was reported even before mefloquine licensure was completed. There is, thus, an urgent need for antimalarial agents which can be used in the treatment of drug-resistant malarial diseases.

Recently it was reported that imipramine and amitriptyline suppress weakly, P. falciparum growth., possibly by virtue of the ability of these agents to interfere with riboflavin metabolism. While scientifically interesting, the practical use of imipramine and amitriptyline in the treatment of malaria would seem unlikely because of the lethal concentrations required to produce the antimalarial effect in humans. While not practically useful in the treatment of non drug-resistant malaria, applicants have now discovered that desipramine, when administered in normal therapeutic doses in conjunction with standard antimalarial agents, is highly effective in treating drug-resistant malaria and is useful in the prophylaxis of drug-resistant malaria.

SUMMARY OF THE INVENTION

Applicants have found that desipramine (Formula 1)

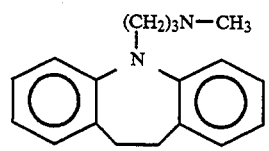

Formula 1 or a pharmaceutically acceptable salt thereof when administered conjunctively with chloroquine, or a pharmaceutically acceptable salt thereof, is useful in the treatment of individuals suffering from drug-resistant Plasmodium infections. More specifically, Applicants have found that administering synergistically effective amounts of chloroquine and desipramine, or pharmaceutically acceptable salts thereof, sufficient to achieve plasma concentration of 50 to 250 ng/ml of desipramine and 3 to 100 ng/ml of chloroquine is an effective method for treating a drug-resistant plasmodium infection.

DETAILED DESCRIPTION OF THE INVENTION

Figure 1:
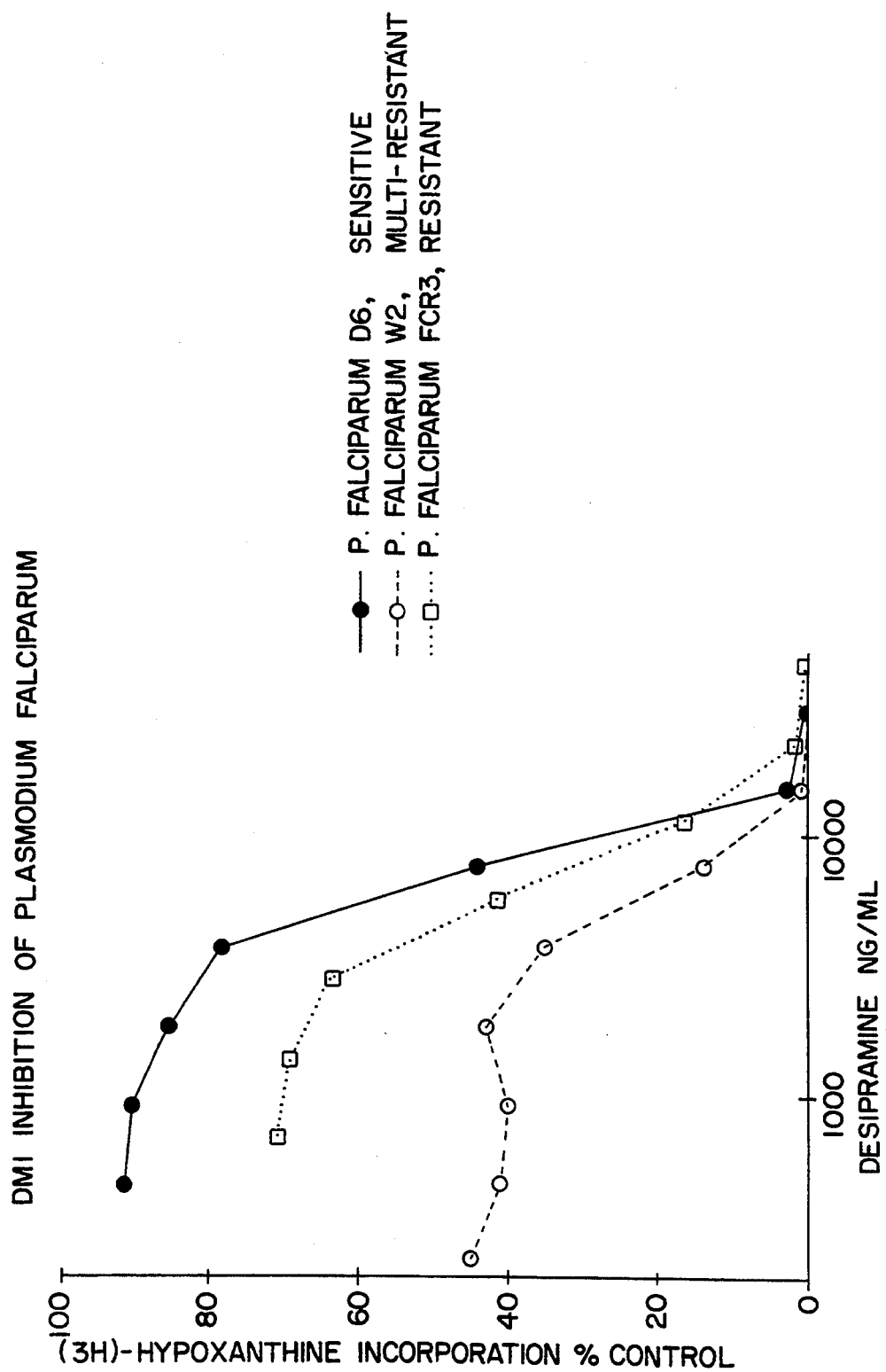

Desipramine, the compound of this invention is well known and is a member of the class of antidepressant compounds referred to as the tricyclic antidepressant compounds. Desipramine is widely available or can be readily prepared by those of ordinary skill in the art of preparing benzocyclic compounds.

Desipramine is preferred above all other compounds for use in the methods of this invention. Prophylactic therapy of malarial infections is normally accomplished by administration of the antimalarial agent in a once or twice a week dosage form. When desipramine is administered in conjunction with an antimalarial agent for malaria prophylaxis, it is preferable to employ a compound which has a comparable blood plasma half-life or which can be administered in a sustained dosage form. For example, chloroquine is administered once a week for prophylaxis of malarial infections. When selecting a compound for conjunctive administration with chloroquine for drug-resistant malaria prophylaxis, a compound with a long plasma half-life such as desipramine is preferred.

The compound of this invention is useful both in the free base form and in the form of acid addition salts. The acid addition salts are simply a more convenient form for use and, in practice, use of the salt amounts to use of the free base. The expression "pharmaceutically acceptable acid addition salts" is intended to apply to any nontoxic organic or inorganic acid addition salts of the base compounds of Formula 1.

The most important use contemplated for the present invention is its use in the treatment of drug-resistant Plasmodium infections (including infections by such species as vivax, malariae, ovale and falciparum), but especially malarial infections of drug-resistant strains of P. falciparum, in humans. The term "drug-resistant malaria" means a malarial infection, particularly of malaria resulting from infection by P. falciparum in humans, which are substantially not responsive to treatment or prophylaxis with existing therapeutic and prophylactic agents such as quinine, chloroquine, amodiaquine, primaquine, or mefloquine.

The antimalarial agents used in the combination therapy or prophylaxis of this invention include any therapeutic or prophylatic agent used in the treatment or prophylaxis of non drug-resistant malarial infections. As used herein, the term "antimalarial agent" specifically does not include the compound of desipramine. Examples of antimalarial agents used in the treatment or prophylaxis of malarial infections are various quinoline derivatives such as quinine, chloroquine, primaquine, sulfadoxine, mefloquine, and pyrimethamine.

The term "conjunctive" when to describe the treatment or prophylaxis of this invention, contemplates the administration of desipramine immediately prior to, concomitantly with, or subsequent to treatment with the antimalarial agent or agents. Applicants contemplate that the tricyclic antidepressant of this invention may be formulated into a single dosage form together with the antimalarial agent; however, such a combination dosage form is not required in order to practice the method of this invention, and no advantage results from use of such a combination product. Rather, because the antimalarial agents and desipramine are widely available in separate dosage forms, applicants expect that patients will be treated using such available, separate dosage forms although a combination dosage form is contemplated especially for the prophylaxis of drug-resistant protozoal infections. Typically, treatment of a patient infected with a drug-resistant malaria, requires doses of the antimalarial agent or agents many times the normal dosage, and such therapy is heroic in nature, i.e., in an effort to save the life of the patient, doses of antimalarial agents normally regarded as "overdosages" are used and symptomatic relief of overdosage symptoms are tended to on an individual basis. While the conjunctive therapy and prophylaxis of this invention will provide for use of less antimalarial agent than would be possible in the absence of desipramine, applicants contemplate that the dose of antimalarial agent employed in the method of this invention will be essentially that dose which would be employed in the absence of the desipramine when used in the treatment or prophylaxis of a non drug-resistant malarial infection. Rather than decreasing the dose of antimalarial agent required, the conjunctive therapy and prophylaxis of this invention will provide for treatment or prophylaxis of malarial infections which would otherwise not be adequately treated or prevented in the absence of a desipramine. In fact, it is the very gist of applicants'discovery that malarial infections which are not responsive to therapy or prophylaxis with standard antimalarial agents, become sensitive to such therapy or prophylaxis when administered in conjunction with desipramine.

Applicants also contemplate that individual dosage forms of an antimalarial agent and a desipramine can be packaged together, with printed instructions for the use of the agents in treating or preventing malarial infections. This would be particularly useful for the prophylactic administration of the agents to individuals traveling to areas where, for example, malaria is endemic. In a preferred embodiment discreet dosage forms of an antimalarial agent and a desipramine are packaged together in a blister pack.

The preferred route of administration is oral administration. For oral administration the compound can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compound of this invention can be tableted with conventional tablet bases such as lactose, sucrose, and cornstarch in combination with binders such as acacia, cornstarch, or gelatin, disintegrating agents intended to assist the breakup and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the esthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The compound of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl- $\beta$-aminopropionates, and 2-alkylimidazoline quaternary ammonium salts, as well as mixtures. The parenteral compositions of this invention will typically contain from about 0.5 to about 25% by weight of the active ingredient in solution. Preservatives and buffers may also be used advantageously. In order to minimize or eliminate irritation at the site of infection, such compositions may contain a nonionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

Pharmaceutical compositions of desipramine and of the antimalarial agents are widely available and can be used in the practice of this invention. Commonly available dosage forms of the desipramine contain from 5 to 250 mg and are to be administered to a human patient from 1 to 3 or 4 times daily, as required. Such dosage forms and frequency of administration are suitable for use in practicing the method of this invention. Pharmaceutical compositions of antimalarial agents such as chloroquine are also widely available and can be used in the practice of the method of this invention. Combination dosage forms, those containing both desipramine and an antimalarial agent are also specifically contemplated for use in the methods of this inventions particularly in the prophylactic methods of this invention.

The ability of the compounds of Formula 1 to treat drug-resistant malarial infections can be demonstrated by following the incorporation of [$^3$H]-hypoxanthine 16, 710–718) into drug-resistant *Plasmodium falciparum* using standard techniques. *P. falciparum* (clone D6, chloroquine-sensitive; strain FCR3, chloroquine-resistant; and clone W2, multi-drug resistant) was grown in vitro by the method of Trager and Jensen, (1976) *Science* 193, 673–675.

FIG. 1 illustrates the effect of desipramine on the inhibition of parasite growth. The degree of sensitivity or resistance of the parasites to chloroquine was found to be inversely related to the sensitivity of the parasites to desipramine.

Figure 2:
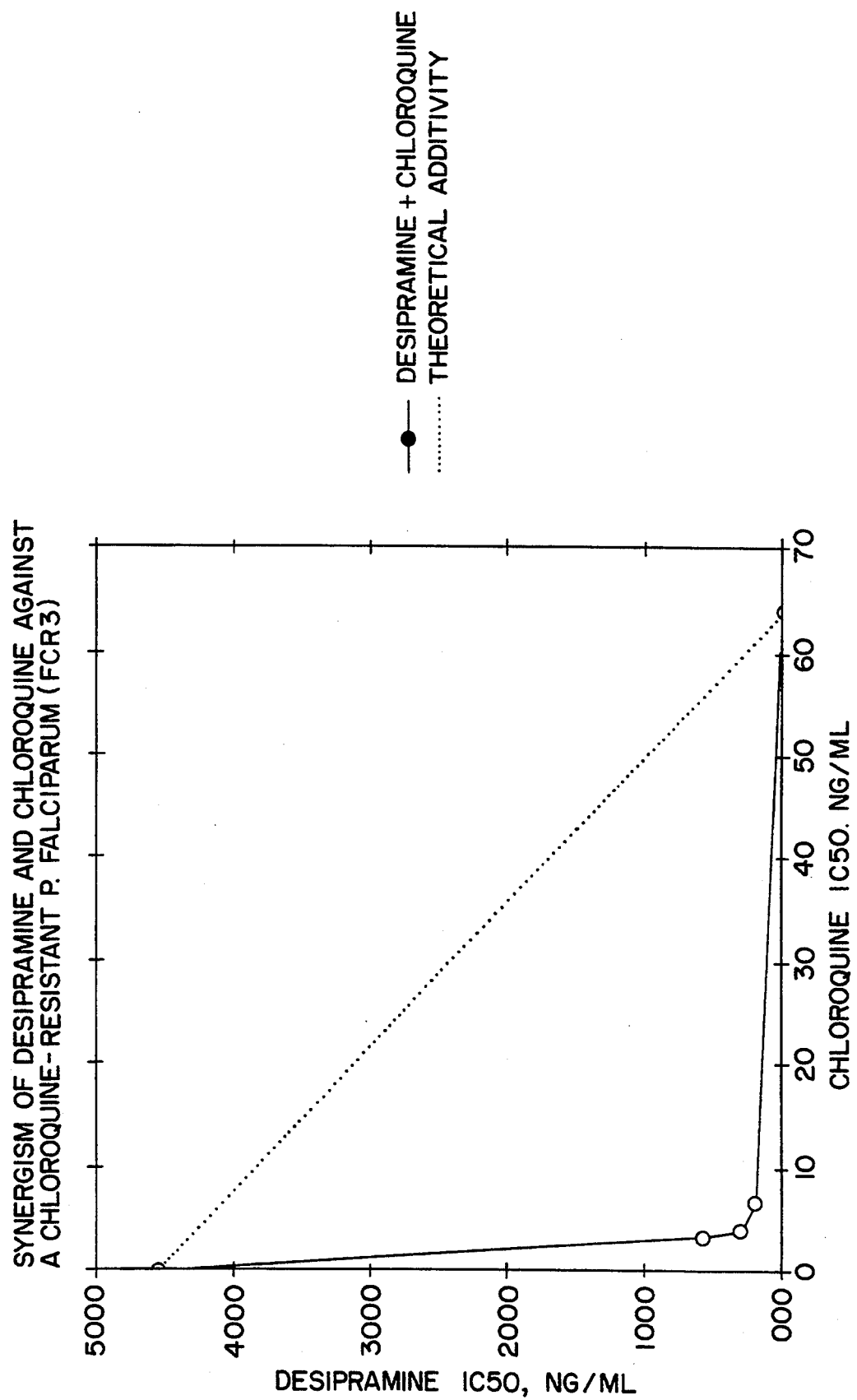

FIG. 2 illustrates the synergism of desipramine and chloroquine against chloroquine-resistant *P. falciparum* (FCR3). Isobologram analysis was carried out according to the method of Martin, et al., (1987) *Science* 235, 899–901 and Berenbaum, (1978) *Journal of Infectious Diseases* 137, 122–130. Drug synergy in this test is demonstrated when a test curve (solid line, desipramine +chloroquine) falls to the left of the theoretical additivity line as is the case with the desipramine +chloroquine curve. The X-axis is the $IC_{50}$ (concentration of drug which inhibits hypoxanthine incorporation by 50%) of chloroquine in the absence or presence of desipramine while the Y-axis is the $IC_{50}$ for desipramine in the absence or presence of chloroquine. The more highly synergistic a combination is, the closer to the origin the points will fall. The combination of desipramine and chloroquine is shown to be highly synergistic.

Figure 3:
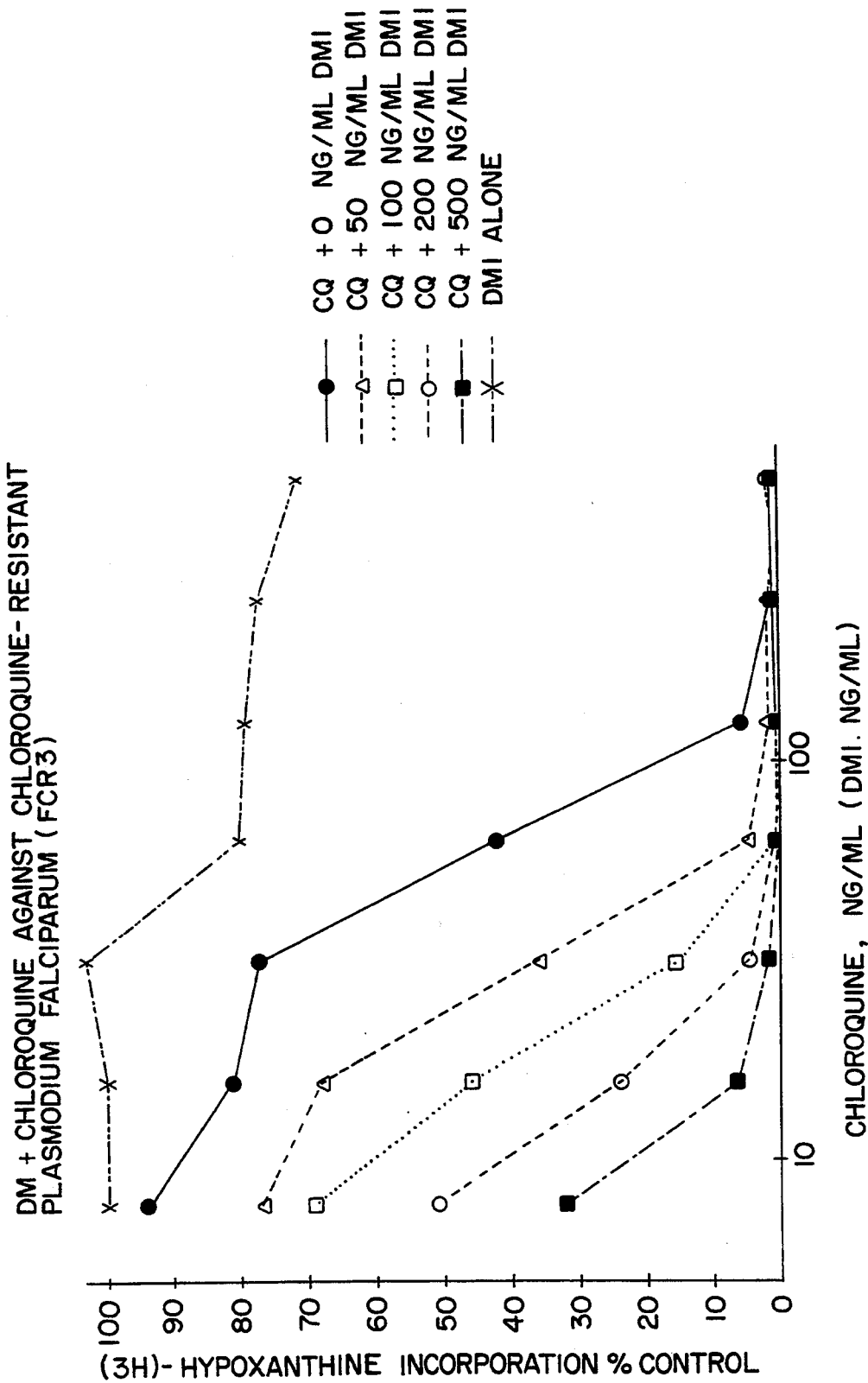

FIG. 3 illustrates the ability of desipramine to enhance the potency of chloroquine against *P. falciparum* (FCR3). Dose-response curves and $IC_{50}$'s for chloroquine were determined either in the absence of desipramine or in the presence of a fixed concentration of desipramine ranging from 50 ng desipramine/ml up to 500 ng desipramine/ml. As the concentration of desipramine was increased the dose-response curves shifted to the left, thus indicating that desipramine enhanced the potency of chloroquine. Clinically achievable plasma concentrations of desipramine in depressed patients are in the range of 50–200 ng/ml. Desipramine (500 ng/ml) lowered the $IC_{50}$ and $IC_{90}$ for chloroquine by 10-fold. An $IC_{50}$ for a chloroquine-sensitive *P. falciparum* strain would be approximately 5 ng/ml. Therefore in the presence of clinically relevant concentrations of desipramine, the chloroquine-resistant *P. falciparum* strain is as sensitive to chloroquine as is the "sensitive" strain. Chloroquine $IC_{50}$'s and $IC_{90}$'s as a function of desipramine concentration are tabulated in Table 1.

TABLE 1

EFFECT OF VARYING DESIPRAMINE CONCENTRATION ON THE SENSITIVITY OF CHLOROQUININE-RESISTANT *P. FALCIPARUM* (FCR3) TO CHLOROQUINE

| Desipramine Concentration (ng/ml) | Chloroquine Inhibitory Concentration (ng/ml) | |
|---|---|---|
| | $IC_{50}$ (ng/ml) | $IC_{90}$ (ng/ml) |
| 0 | 52 | 110 |
| 50 | 25 | 52 |
| 100 | 15 | 39 |
| 200 | 8 | 25 |
| 500 | <5 | 14 |

Figure 4:
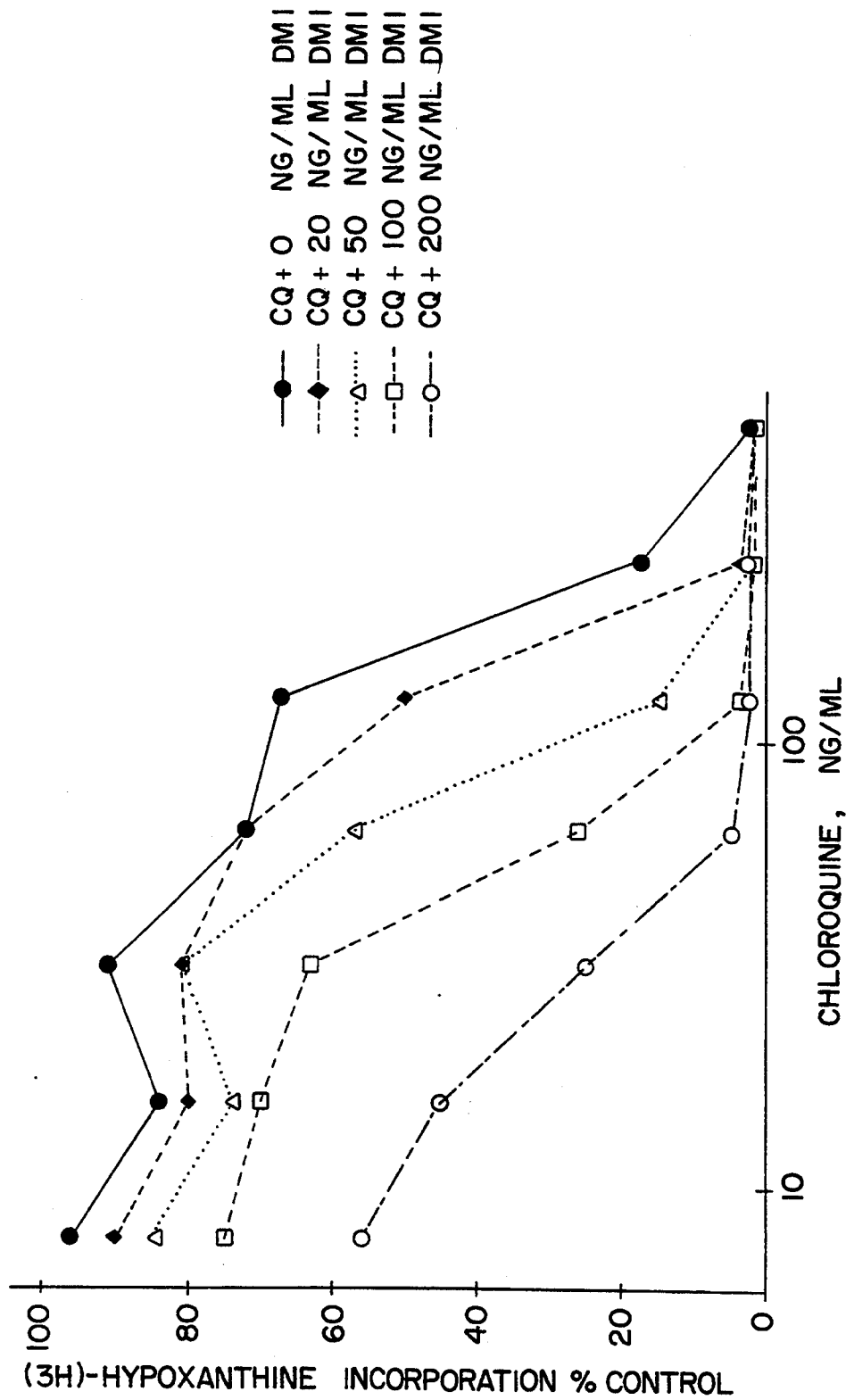

FIG. 4 illustrates the ability of desipramine to enhance the potency of chloroquine against *P. falciparum* (W2). The experiment is identical to that of FIG. 3 but a different strain of *P. falciparum* was used. The W2 strain is more sensitive to desipramine. The $IC_{50}$ and $IC_{90}$ for chloroquine are lowered by a factor of approximately 10. The concentrations of desipramine used have only slight effects of *P. falciparum* when desipramine was added alone. Chloroquine $IC_{50}$'s and $IC_{90}$'s as a function of desipramine concentration are tabulated in Table 2.

TABLE 2

EFFECT OF VARYING DESIPRAMINE CONCENTRATION ON THE SENSITIVITY OF CHLOROQUININE-RESISTANT *P. FALCIPARUM* (W2) TO CHLOROQUINE

| Desipramine Concentration (ng/ml) | Chloroquine Inhibitory Concentration (ng/ml) | |
|---|---|---|
| | $IC_{50}$ (ng/ml) | $IC_{90}$ (ng/ml) |
| 0 | 160 | 300 |
| 20 | 120 | 220 |
| 50 | 70 | 150 |
| 100 | 40 | 92 |
| 200 | 12.5 | 50 |

Figure 5:
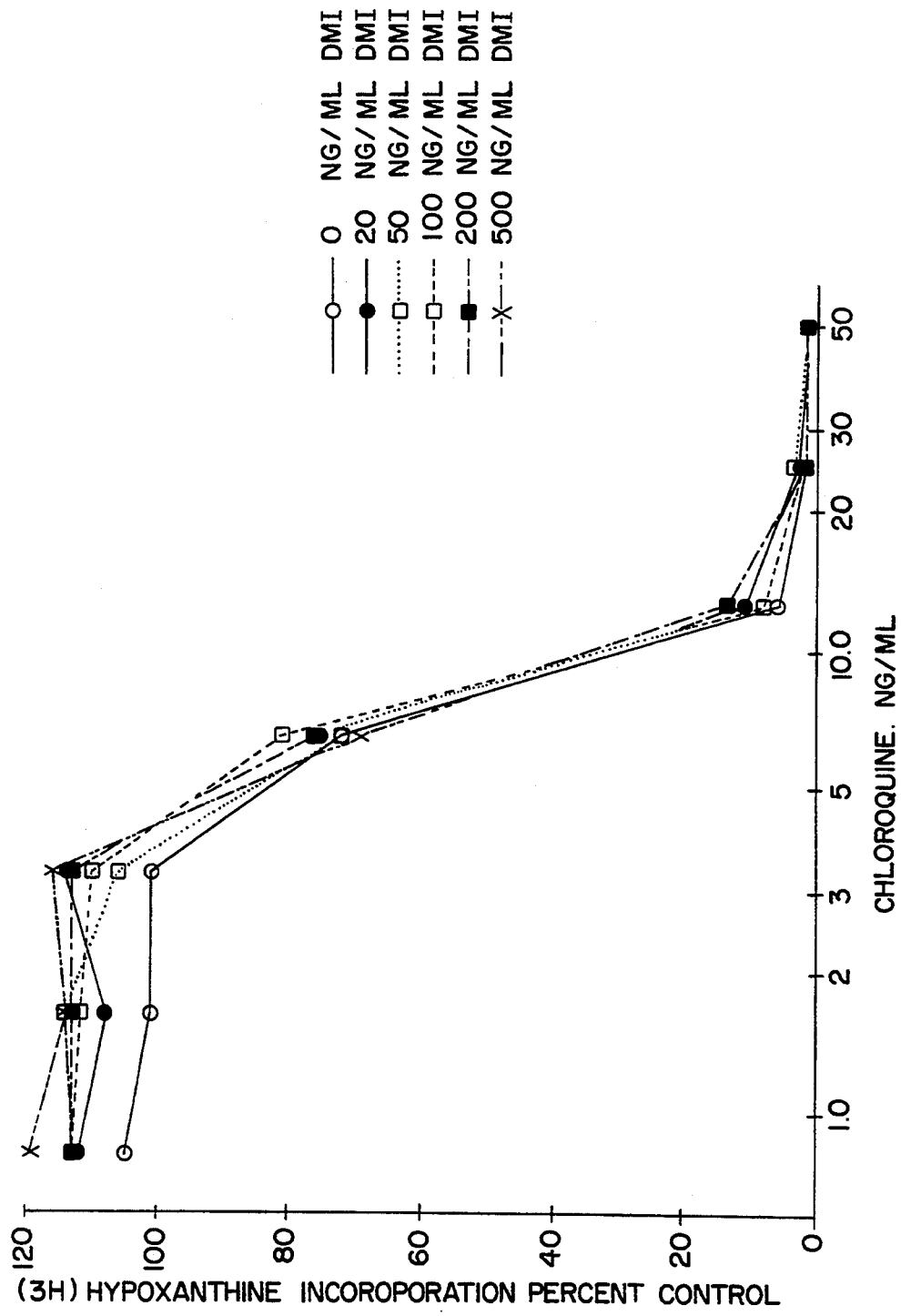

FIG. 5 illustrates that desipramine does not change the response of the chloroquine-susceptible clone D6 of *P. falciparum* to chloroquine in an experiment similar to those in FIGS. 3 and 4.

Figure 6:
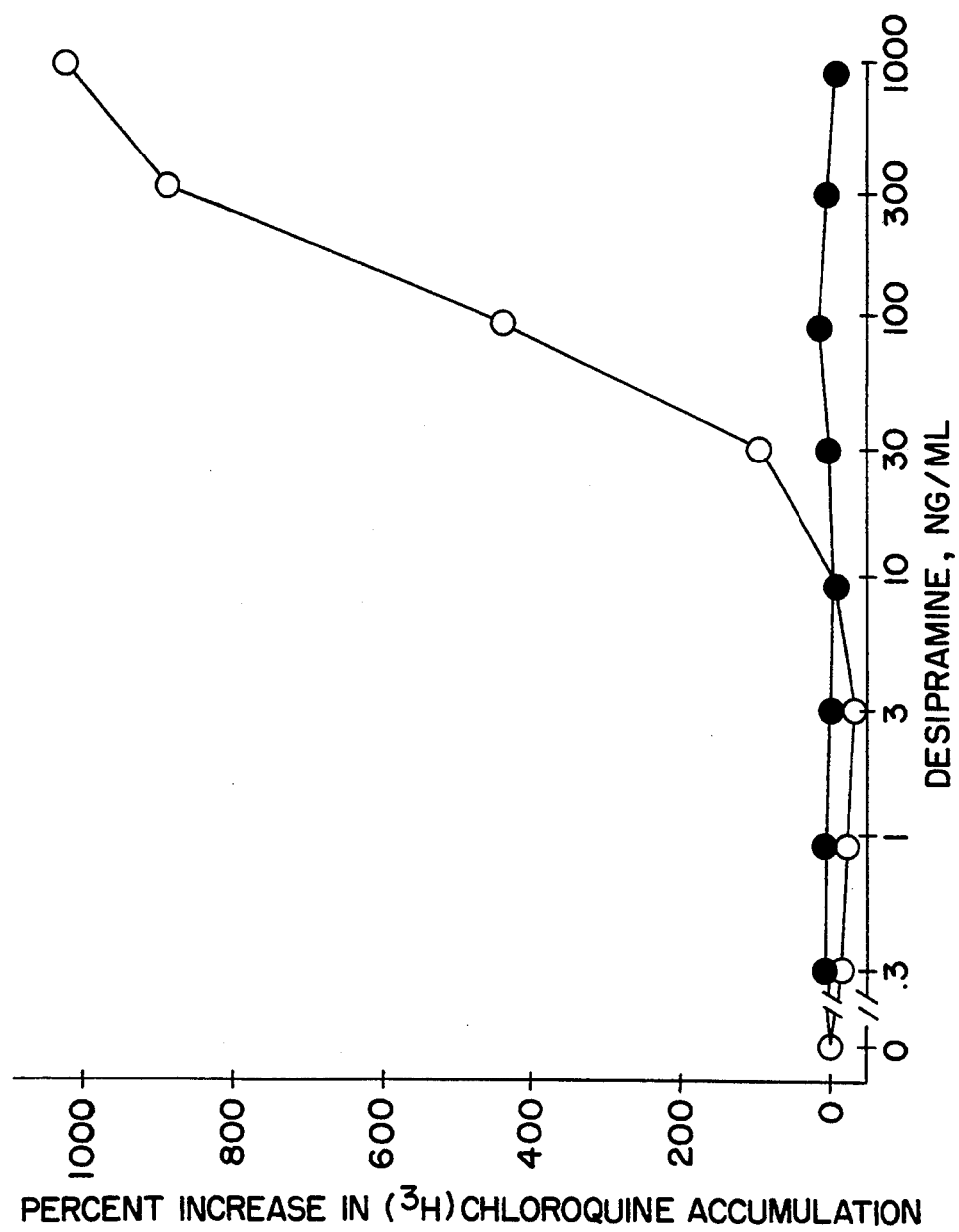
Figure 7:
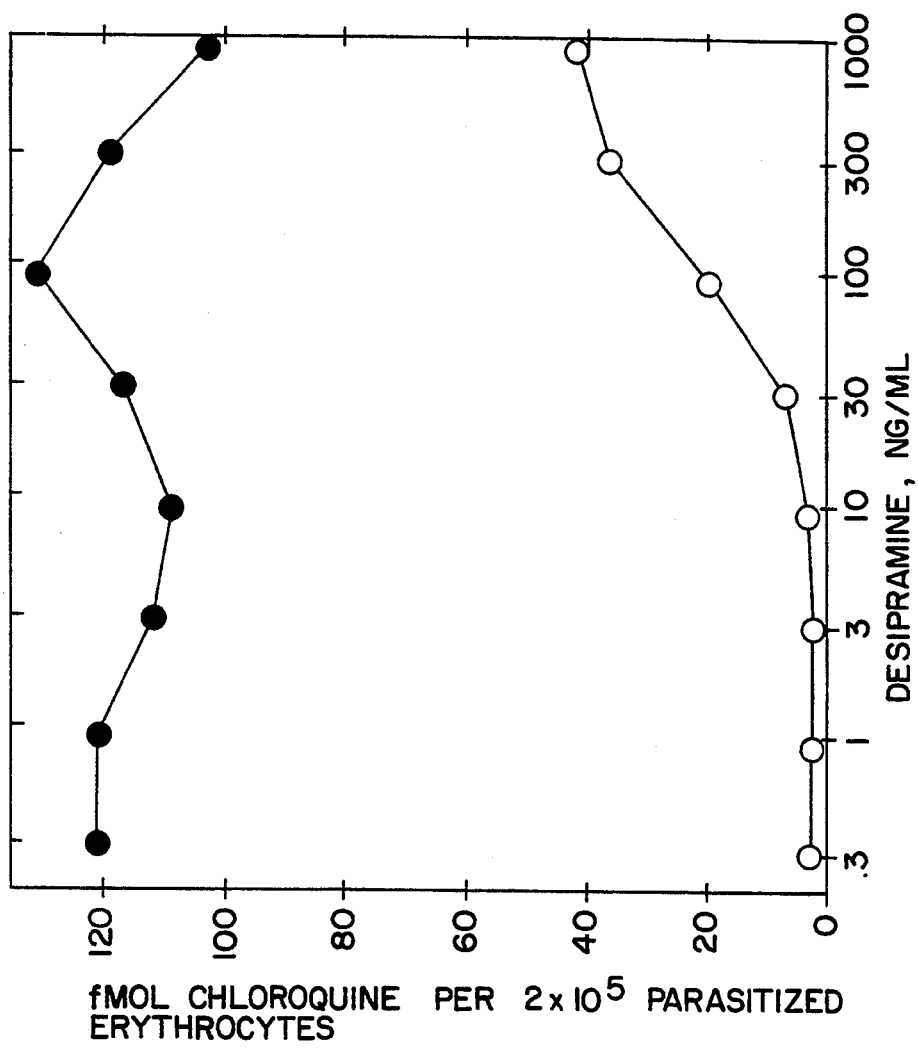

FIG. 6 and FIG. 7, Desipramine increases the accumulation of chloroquine by drug-resistant *P. falciparum* but not by drug-susceptible parasites. Uptake of [3H]-chloroquine was followed in clone D6 (chloroquine susceptible, •) and in clone W2 (multi-drug resistant, o) in the absence or presence of desipramine.

EXAMPLES

The following example is intended to illustrate, but not to limit in any way, the compositions useful in the methods of this invention.

EXAMPLE 1

Tablets

Tablets were prepared in the usual manner each having the composition:

| | |
|---|---|
| Chloroquine phosphate | 250 mg |

-continued

| | |
|---|---|
| Desipramine HCl | 75 mg |
| Dibasic calcium phosphate | 50 mg |
| Lactose | 250 mg |
| Magnesium stearate | 10 mg |
| Starch | 100 mg |

What is claimed is:

1. A method of treating a drug-resistant Plasmodium infection in a patient in need thereof which comprises administering to the patient synergistically effective amounts of chloroquine and desipramine, or pharmaceutically acceptable salts thereof, sufficient to achieve plasma concentrations of 50 to 250 ng/ml of desipramine and 3 to 100 ng/ml of chloroquine.

* * * * *

UNITED STATES PATENT AND TRADEMARK OFFICE
CERTIFICATE OF CORRECTION

PATENT NO. : 5,373,005

DATED : December 13, 1994

INVENTOR(S) : Alan, J. Bitonti, Peter P. McCann, Albert Sjoerdsma

It is certified that error appears in the above-identified patent and that said Letters Patent is hereby corrected as shown below:

On the cover page and also at column 1, line 1 the patent reads "Despiramine" and should read --Desipramine--.

At column 4, line 22, reads "acceptably" and should read --acceptable--.

At column 4, line 66, reads "infection" and should read --injection--.

At column 5, lines 28-29, reads "hypoxanthine 16," and should read --hypoxanthine (Desjardins, et al., (1979) Antimicrobial Agents Chemotherapy 16--.

In Figure 3, line 1 reads "DM +" and should read -- DMI + --

Signed and Sealed this

Twenty-sixth Day of September, 1995

Attest:

BRUCE LEHMAN

*Attesting Officer*  *Commissioner of Patents and Trademarks*